US009987436B2

(12) United States Patent
Giambattista et al.

(10) Patent No.: US 9,987,436 B2
(45) Date of Patent: Jun. 5, 2018

(54) MEDICAMENT DELIVERY DEVICE

(71) Applicant: Carebay Europe Ltd, Swatar (MT)

(72) Inventors: Lucio Giambattista, Lighthouse Point, FL (US); Antonio Bendek, Wellington, FL (US); Mattias Daniel, Stockholm (SE); Sebastian Karlsson, Sundbyberg (SE)

(73) Assignee: Carebay Europe Ltd, Sliema (MT)

( * ) Notice: Subject to any disclaimer, the term of this patent is extended or adjusted under 35 U.S.C. 154(b) by 263 days.

(21) Appl. No.: 14/654,520

(22) PCT Filed: Dec. 6, 2013

(86) PCT No.: PCT/EP2013/075789
§ 371 (c)(1),
(2) Date: Jun. 20, 2015

(87) PCT Pub. No.: WO2014/095424
PCT Pub. Date: Jun. 26, 2014

(65) Prior Publication Data
US 2015/0335829 A1    Nov. 26, 2015

Related U.S. Application Data

(60) Provisional application No. 61/745,053, filed on Dec. 21, 2012.

(30) Foreign Application Priority Data

Dec. 21, 2012  (SE) ........................... 1251499

(51) Int. Cl.
*A61M 5/32* (2006.01)
*A61M 5/20* (2006.01)
(Continued)

(52) U.S. Cl.
CPC ........ *A61M 5/3204* (2013.01); *A61M 5/2033* (2013.01); *A61M 5/3146* (2013.01);
(Continued)

(58) Field of Classification Search
CPC .... A61M 2005/2013; A61M 2005/206; A61M 2005/208; A61M 2005/2073;
(Continued)

(56) References Cited

U.S. PATENT DOCUMENTS 7,794,432 B2    9/2010 Young et al.
2012/0265136 A1*  10/2012 Lawlis ................. A61K 38/24
604/110

(Continued)

FOREIGN PATENT DOCUMENTS

GB          2447787 A       9/2008
WO      2007/131013 A1    11/2007
(Continued)

OTHER PUBLICATIONS

EPO, Int'l Search Report in PCT/EP2013/075789, dated Apr. 2014.
EPO, Written Opinion in PCT/EP2013/075789, dated Apr. 2014.

*Primary Examiner* — Quynh-Nhu H Vu
(74) *Attorney, Agent, or Firm* — Piedmont Intellectual Property

(57) ABSTRACT

A medicament delivery device includes a housing having proximal and distal ends; a delivery member connected to the housing; a medicament container operably arranged within the housing; a drive mechanism configured to act on the medicament container for priming and for expelling a dose of medicament; and an activator mechanism configured to interact with the drive mechanism, such that a first interaction between the activator mechanism and the drive mechanism causes the container to move toward the delivery member, in which the container is primed, and such that a
(Continued)

subsequent interaction between the activator mechanism and the drive mechanism causes a dose of medicament to be expelled through the delivery member.

19 Claims, 12 Drawing Sheets

(51) Int. Cl.
    *A61M 5/31*     (2006.01)
    *A61M 5/24*     (2006.01)

(52) U.S. Cl.
    CPC ....... *A61M 5/326* (2013.01); *A61M 2005/206* (2013.01); *A61M 2005/2013* (2013.01); *A61M 2005/2073* (2013.01); *A61M 2005/247* (2013.01)

(58) Field of Classification Search
    CPC .......... A61M 2005/247; A61M 5/2033; A61M 5/3146; A61M 5/3204; A61M 5/326
    See application file for complete search history.

(56) References Cited

U.S. PATENT DOCUMENTS

2013/0324934 A1* 12/2013 Holmqvist .......... A61M 5/2033
    604/192
2014/0228769 A1* 8/2014 Karlsson ............. A61M 5/2033
    604/197

FOREIGN PATENT DOCUMENTS

| WO | 2012/003516 A2 | 1/2012 |
| WO | 2012/022810 A2 | 2/2012 |
| WO | 2012/025639 A1 | 3/2012 |

\* cited by examiner

MEDICAMENT DELIVERY DEVICE

TECHNICAL AREA

The present invention relates to a medicament delivery device displaying a high degree of safety, security and readiness.

BACKGROUND OF INVENTION

A large number of medicament delivery devices for self-administration have been developed the last decades. Many of these devices utilize injection needles that penetrate the skin of the patient for delivery of a dose.

Some devices have automatic mechanisms for penetration and subsequent injection of medicament. While providing a degree of automation and less manual handling by the patient, some persons feel uneasy using such devices, for instance when they cannot fully control penetration and/or injection.

During the years, a number of the devices have used syringes as medicament containers where an injection needle is an integral part of the container. The distal end of the injection needle is in constant contact with the medicament and the needle is tubular, i.e. there is a small passage through the needle.

For some types of medicament, or for some applications, such an arrangement is unsuitable since air may enter through the passage of the needle and may adversely affect the medicament. Also, the injection needle and/or the medicament can be adversely affected by the contact between the metal of the needle and the chemicals of the medicament.

Other types of common medicament containers are so called medicament cartridges, which have a neck or connection portion at one end of the container, where the neck portion often is arranged with a penetrable wall, a septum. A suitable injection needle is then connected to the neck portion, where the connection members may comprise threads, bayonet fittings, luer locks, just to mention a few. The advantage is that the interior of the medicament container, or cartridge, and its contents are sealed off from the environment until an injection needle is attached and the septum is pierced.

A drawback of this solution is that a user or patient has to perform assembly steps in order to attach the injection needle to the cartridge, which may be difficult for some persons who suffer from reduced manual dexterity, etc. Also, if there is an emergency situation where a patient or user needs his/her medication quickly, assembly steps may be very disturbing and stressful. Further, attachment of an injection needle to a cartridge most often requires a subsequent placement of the assembled needle/cartridge in a medicament delivery device since it is much easier to perform the assembly outside the medicament delivery device. Thus, further handling steps are required before the device is ready to deliver a dose.

In order to handle these drawbacks, some devices have been developed such that during activation, the connection of an injection needle to a cartridge type medicament container is achieved.

For example, document WO 2012/022810 discloses a device where an injection needle having a proximal pointed end and a distal pointed end is arranged inside a device, and wherein a medicament cartridge is brought in contact with the distal pointed end when the device is to be used. Before use, both ends of the injection needle are kept sterile by protective sheaths. These sheaths are pierced and compressed during use of the device.

A drawback of this device is that the handling sequence is not optimal. '810 describes that a penetration step with the proximal end of the injection needle is performed before the distal end penetrates the septum of the cartridge. During the penetration step, a contactor is pushed in the distal direction, exposing the injection needle. The end of the penetration should then first trigger a penetration of the septum and should then trigger a subsequent release of the plunger rod for expelling a dose of medicament. Thus, there is no priming of the medicament container before injection, and there are several steps that need to be performed after penetration in order to provide an injection. Further, the safety aspects are minimal in that only a cover has to be removed before the device is ready and active. There is no further mechanism for locking the contactor until use and there is therefore a risk that someone may be pricked by accidentally pushing the contactor in the distal direction.

Another document describing the handling of the above mentioned drawbacks is WO 2012/025639. It discloses a number of embodiments of a device comprising an injection needle with both distal and proximal pointed ends, wherein a medicament container is pierced only when the device is to be used. The document does not deal with any enhanced safety aspects and some of the embodiments do not have any means for shielding or protecting the injection needle before or after use.

Regarding safety aspects, document U.S. Pat. No. 7,794,432 discloses a medicament delivery device provided with a safety mechanism in the form of a safety pin arranged at a distal end of the device. The safety pin is designed to engage a collet of a power pack such that it prevents the end of the collet from compressing, in turn preventing actuation of the device. When the device is to be used, the safety pin is removed whereby the device is ready for actuation.

The safety pin of '432 is a simple blocking member that does not perform any other actions than preventing compression of the collet. When removed, the collet could be compressed by rough handling of the device, leading to unintentional premature dose delivery. Further, the device of '432 is arranged with a conventional medicament container, leading to the above mentioned problems.

BRIEF DESCRIPTION OF INVENTION

In the present application, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axial", or "axially", refer to a direction, or an axis, through the device or components thereof in the direction of the longest extension of the device or the component. In a similar manner, the term "lateral", with or without "axis", refers to a direction or an axis through the device or components thereof in a direction generally perpendicular to the longitudinal direction. Also, if nothing else is stated, in the following description wherein the mechanical structure of the device and the mechanical interconnection of its components is described, the device is in an initial non-activated or non-operated state.

The aim of the present invention is to remedy the drawbacks of the state of the art medicament delivery devices. This aim is solved by a device according to the features of the independent patent claim. Preferable embodiments of the invention form the subject of the dependent patent claims.

According to a main feature of the present invention, it relates to a medicament delivery device comprising a housing having a proximal and a distal end, arranged to accommodate a medicament container. Preferably a drive mechanism is arranged in the device, capable of acting on the medicament container for priming and for expelling a dose of medicament through a delivery member. The device further comprises an activator mechanism configured to interact with the drive mechanism, such that a first interaction between the activator mechanism and the drive mechanism causes the container to move towards the delivery member wherein the container is primed and such that a subsequent second interaction between the activator mechanism and the drive mechanism causes a dose of medicament to be expelled through the delivery member.

According to another feature of the present invention, the activator mechanism is configured such that the second interaction is prevented from being achieved until the first interaction is achieved.

According to yet another feature of the present invention, the activator mechanism comprises a contactor operably arranged to the housing at a proximal end thereof; a rotator operably arranged inside the housing and operably connected to the contactor and to the drive mechanism; and a safety member operably arranged to the housing at a distal end thereof and operably connected to the rotator. Preferably, the activator mechanism comprises a contactor slidably arranged to the housing at a proximal end thereof; a rotator rotatably arranged inside the housing and operably connected to the contactor and to the drive mechanism; and a safety member releasably arranged to the housing at a distal end thereof and operably connected to the rotator. More preferably, the activator mechanism comprises a contactor rotationally locked and slidably arranged to the housing at a proximal end thereof; a rotator slidably locked and rotatably arranged inside the housing and operably connected to the contactor and to the drive mechanism; and a safety member rotatably locked and releasably arranged to the housing at a distal end thereof and operably connected to the rotator.

The intension of the contactor is to be brought in contact with a dose delivery site of a patient or user during a medicament dose delivery process. In this respect, a rotator is intended to comprise a generally tubular or barrel-shaped body that can be turned inside the housing or the like in order to perform a number of functions. In order to facilitate the performance of different functions, the rotator may be arranged with a number of inner and outer ledges, ridges, guide members or the like that may either control the movement of the rotator and/or the movement of other components and mechanisms interacting with the rotator. In addition to ledges, there may be protrusions, tongues, wedge-shaped ridges and the like components. Further, removal of the safety member for setting the medicament delivery device ready for use causes a rotation of the rotator such that the contactor may rotate the rotator for activating the drive mechanism.

According to a further feature of the present invention, the contactor is axially movable in relation to the housing between an extended position in which the delivery member is hidden and protected by the contactor and a retracted position in which the delivery member is exposed. Preferably, the contactor is longitudinally movable and prevented to be rotated in relation to the housing.

According to yet a further feature of the present invention, there is an interaction between the safety member and the contactor via the rotator wherein the contactor and the rotator are arranged to interact with each other such that the rotator prevents the contactor from being moved from the extended position to the retracted position, until the safety member forces the rotator to rotate, i.e. until the safety member is removed. This ensures that the device is not activated prematurely to priming. When the safety member is in place on the device, this is an indication that the device has not been used. In this aspect, the device is arranged such that the safety member may not be re-attached after removal.

Preferably the first interaction is an interaction between the rotator and the drive mechanism caused by an interaction between the safety member and the rotator, whereby removal of the safety member causes a rotation of the rotator such that the drive mechanism may act on the container for priming the container.

The second interaction is preferably a further interaction between the contactor and the rotator causing a further interaction between the rotator and the drive mechanism, whereby movement of the contactor from the extended to the retracted position causes a further rotation of the rotator such that the drive mechanism may further act on the container for expelling a dose of medicament through the delivery member.

The drive mechanism may preferably comprise a plunger rod and a force member 108 having predetermined load force configured to act on the plunger rod, wherein the plunger rod is operably connected to the rotator such that turning of the rotator by the safety member causes a release of the plunger rod. In other words, the force member is pre-tensioned arranged to the plunger rod. In this aspect, the force member may be any suitable member that is capable of moving the plunger rod. The force member may thus be a compression spiral spring, a gas spring, a resilient material member, a clock spring, just to mention a few.

Preferably the plunger rod may comprise a number of first contact members, and that the rotator comprises a number of inner guiding members interacting with the first contact members for holding the plunger rod in an initial state, an intermediate state and in a final state depending on the rotational angle of the rotator.

Each of the inner guiding members may preferably comprise a first inner longitudinal section, a first inner transversal and circumferential section, an inner inclined section, second inner longitudinal section, a second inner transversal and circumferential section, third inner longitudinal section, and a third inner transversal and circumferential section. Having these features, a number of different functions may be included and performed by a very few number of components. In particular the combined steps of priming and expelling a dose of medicament with an intermediate stop position are readily achieved with the rotator.

Preferably, the plunger rod is held in the initial state due to the interaction between each of the first contact members of the plunger rod and each of the first inner transversal and circumferential sections of the inner guiding members on the inner surface of the rotator until the rotator is turned when the safety member is removed.

Preferably the contactor is operably connected to the rotator such as to turn the rotator and thus the contactor preferably comprises a number of third contact members, and the rotator preferably further comprises second outer guiding members arranged to interact with the third contact members of the contactor.

Each of the second outer guiding members preferably comprises a first outer longitudinal section, a first outer transversal and circumferential section, a second outer longitudinal section, an outer inclined section, a third outer longitudinal section, and a fourth outer longitudinal section which is parallel with the first and second outer longitudinal sections.

Preferably each of the third contact members of the contactor is arranged to interact with each of the first outer transversal and circumferential sections of the second outer guiding members on the outer surface of the rotator such that the contactor is locked from movement until the rotator is turned when the safety member is removed. This feature ensures that the delivery member i.e. injection needle is prevented to be accessed until the device is ready for use.

The safety member preferably comprises second contact members arranged to cooperate with first outer guiding members on the rotator capable of, upon removal of the safety member, turning the rotator a certain rotational angle such that the plunger rod is released from the initial state to an intermediate state for priming the container. The plunger rod is preferably held in the intermediate state due to the interaction between each of the first contact members of the plunger rod and each of the second inner transversal and circumferential sections of the inner guiding members on the inner surface of the rotator.

Preferably, the first outer guiding members on the rotator prevent re-connection of the safety member after removal of the safety member and the turning of the rotator. This gives an indication that the device is already primed.

Further, preferably, the third contact members are arranged to interact with the outer inclined sections whereby movement of the contactor from the extended position to the retracted position causes the further rotation of the rotator a certain rotational angle such that the plunger rod is released from the intermediate state to a final state, expelling a dose of medicament through the delivery member.

Preferably, the plunger rod is held in the final state due to the interaction between each of the first contact members of the plunger rod and each of the third inner transversal and circumferential section of the inner guiding members on the inner surface of the rotator.

Further, the rotator may preferably comprise first lock members arranged to interact with the third contact members of the contactor such that the contactor is locked from axial movement after the dose of medicament is expelled through the delivery member and the contactor is moved from the retracted to the extended position. This ensures that the delivery member i.e. injection needle is covered by the contactor and is not accessible. This avoids unintentional sticks or other injuries caused by the delivery member.

In a preferable embodiment, the delivery member is an injection needle assembly fixedly connected to the housing, wherein the injection needle assembly comprises a hub wherein an injection needle is arranged with a proximal pointed end and a distal pointed end, and wherein the distal pointed end and the proximal pointed end are surrounded and covered with respective protective sheaths. Thereby, the injection needle is protected from contamination before use, and is also kept sterile. Further, the protective sheath covering the distal end is configured to be pierced and compressed during movement of the medicament container. The protective sheath covering the proximal end is configured to be pierced and compressed during movement of the contactor from the extended to the retracted position such that the proximal pointed end of the injection needle is exposed.

According to yet a favourable embodiment of the device, it may further comprise a medicament container holder arranged movable inside the housing and arranged to accommodate the medicament container. Preferably the drive mechanism may be operably connected to, upon activation, move the medicament container holder from a position in non-contact with the injection needle, to a position where the injection needle creates a passage into the medicament container. This solution has the advantage that the injection needle is not in contact with the medicament inside the medicament container until it is time to deliver a dose of medicament. This is important since the medicament may be affected by the material of the injection needle or vice versa, which may otherwise adversely affect both the medicament and the injection needle.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
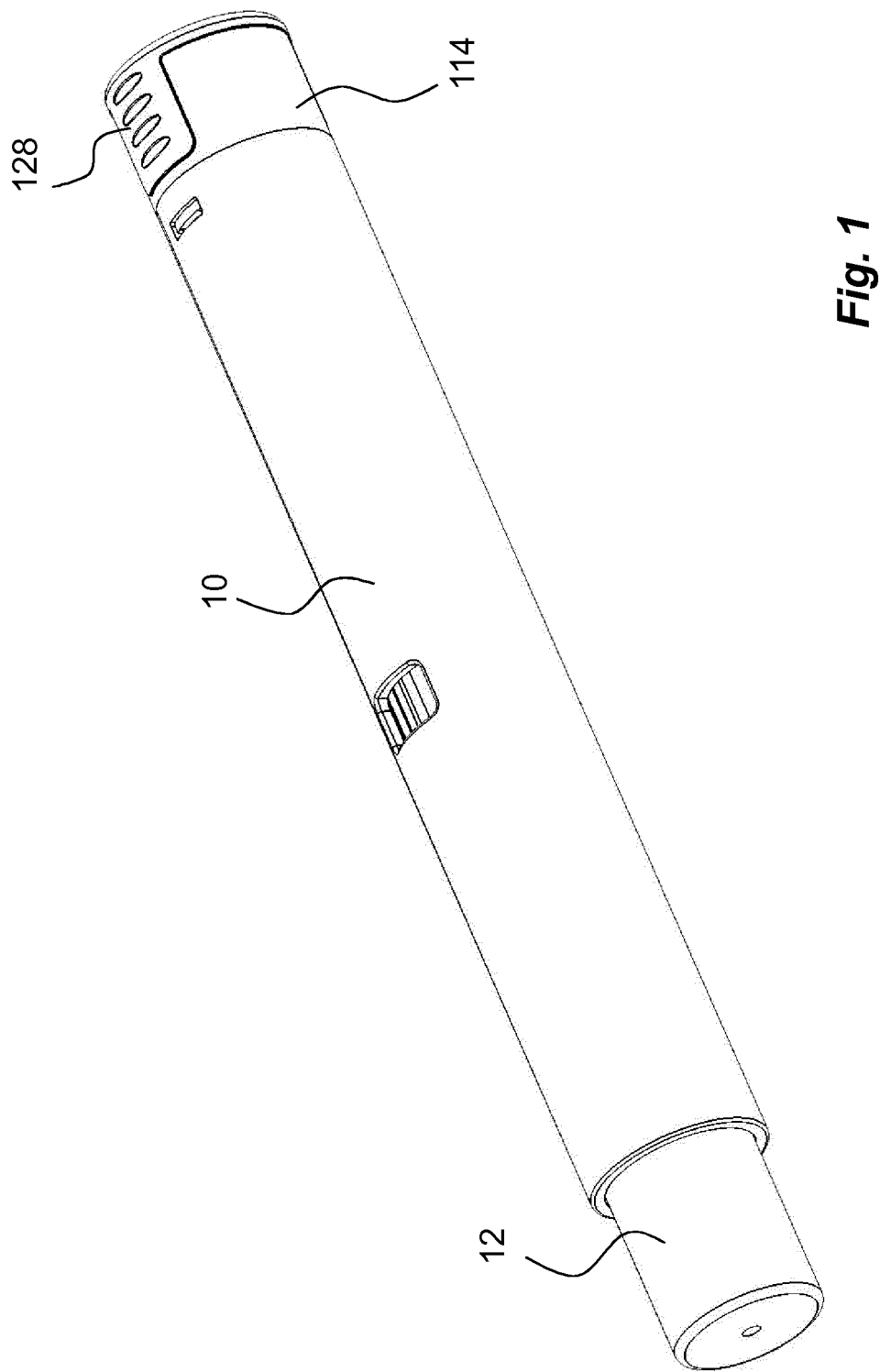
FIG. 1 shows a perspective view of an exemplary embodiment of a medicament delivery device according to the invention.

The exemplary medicament delivery device shown in the drawings comprises a generally elongated housing having proximal and distal ends, a delivery member 40 connected to the housing; a medicament container 84 operably arranged within the housing; a drive mechanism capable of acting on the medicament container for priming and for expelling a dose of medicament; wherein the device further comprises an activator mechanism configured to interact with the drive mechanism, such that a first interaction between the activator mechanism and the drive mechanism causes the container to move towards the delivery member wherein the container is primed and such that a subsequent second interaction between the activator mechanism and the drive mechanism causes a dose of medicament to be expelled through the delivery member.

Further, the activator mechanism is configured such that the second interaction is prevented to be achieved until the first interaction is achieved as it will be explained below.

The housing comprises a tubular first housing part 10, FIG. 1, being open at both ends and a second housing part 114 attached to the distal end of the first housing part. These two housing parts may be considered as one component.

The activator mechanism comprises a contactor 12 operably arranged to the housing at a proximal end thereof; a rotator 82 operably arranged inside the housing and operably connected to the contactor 12 and to the drive mechanism; and a safety member 128 operably arranged to the housing at a distal end thereof and operably connected to the rotator. Further, the contactor is axially movable in relation to the housing between an extended position in which the delivery member is hidden and protected by the contactor and a retracted position in which the delivery member is exposed. The contactor and the rotator are arranged to interact with each other such that the rotator prevents the contactor from being moved from the extended position to the retracted position, until the first interaction is completed.

The first interaction is an interaction between the rotator and the drive mechanism caused by an interaction between the safety member and the rotator, whereby removal of the safety member 128 causes a rotation of the rotator 82 such that the drive mechanism may act on the container for priming the container. This interaction will be explained below in detail.

Figure 2:
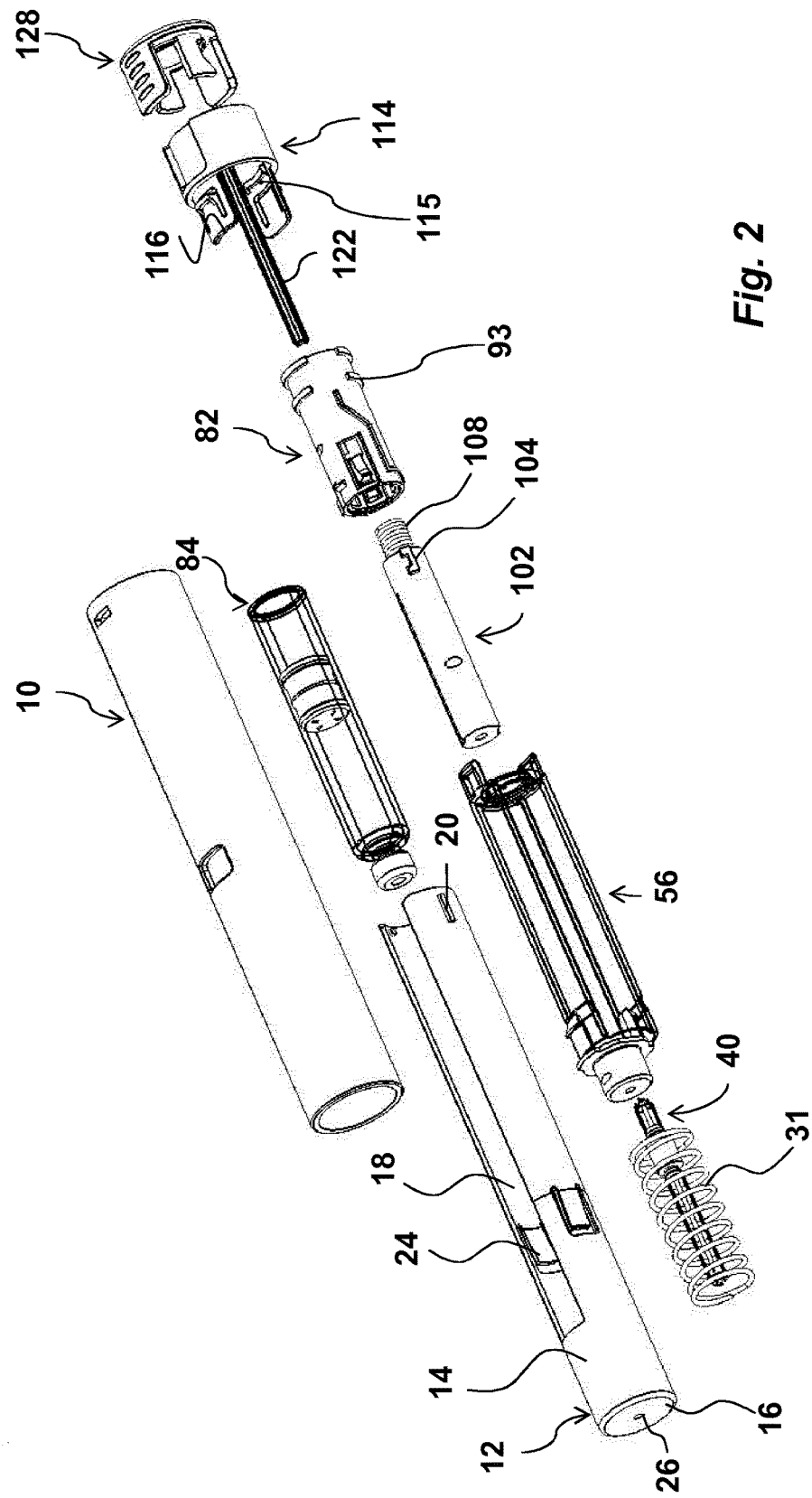
FIG. 2 is an exploded view of the device of FIG. 1.

The contactor 12 is in the embodiment shown as a delivery member cover. The contactor 12 comprises a generally tubular proximal part 14 having a transversal proximal end wall 16, FIG. 2. Two longitudinally extending arms 18, FIG. 4, extend towards the distal end from the tubular part 14. Each of the extending arms 18 has an outer surface with a curvature that generally corresponds to the inner surface of the first housing part 10, whereby the contactor is slidable in the longitudinal direction in relation to the first housing part. The outer surfaces of the arms 18 are arranged with guide ribs 20, FIG. 4, which guide ribs 20 are intended to fit into longitudinally extending grooves 22 on the inner surface of the first housing part 10, FIG. 4, whereby the contactor 12 is guided during longitudinal sliding of the contactor 12 in relation to the first housing part 10 and prevent a rotation of the contactor in relation to the housing. The contactor is arranged within the housing such that the tubular part 14 protrudes from the proximal end of the housing.

Figure 4:
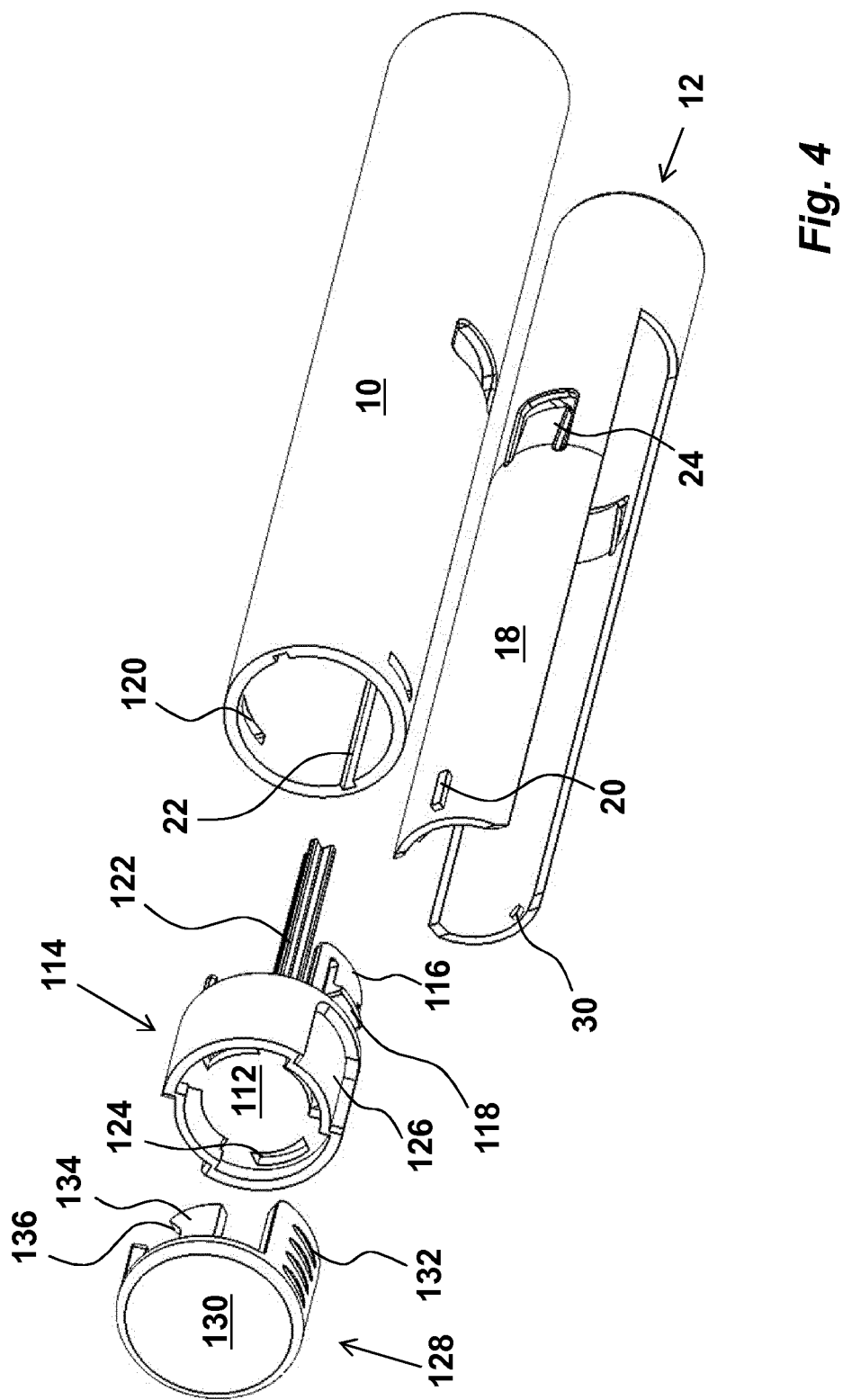

The contactor 12 is further arranged with two generally radially flexing tongues 24, FIG. 4, one on each arm and with the free ends facing the proximal end of the contactor 12. The tongues 24 are arranged such that they have a certain inclination somewhat inwards in their free un-tensioned state. The transversal end wall 16 of the contactor is further provided with a centrally positioned passage 26, FIG. 2, through which a delivery member, such as an injection needle, may pass when the device is used, as will be described. Further, the contactor comprises a number of third contact members 30. Each of the arms 18 of the contactor 12 is arranged with a third contact member 30 which may be a protrusion, FIG. 4, on inner surfaces thereof at a distal end area of the arms.

Figure 5:
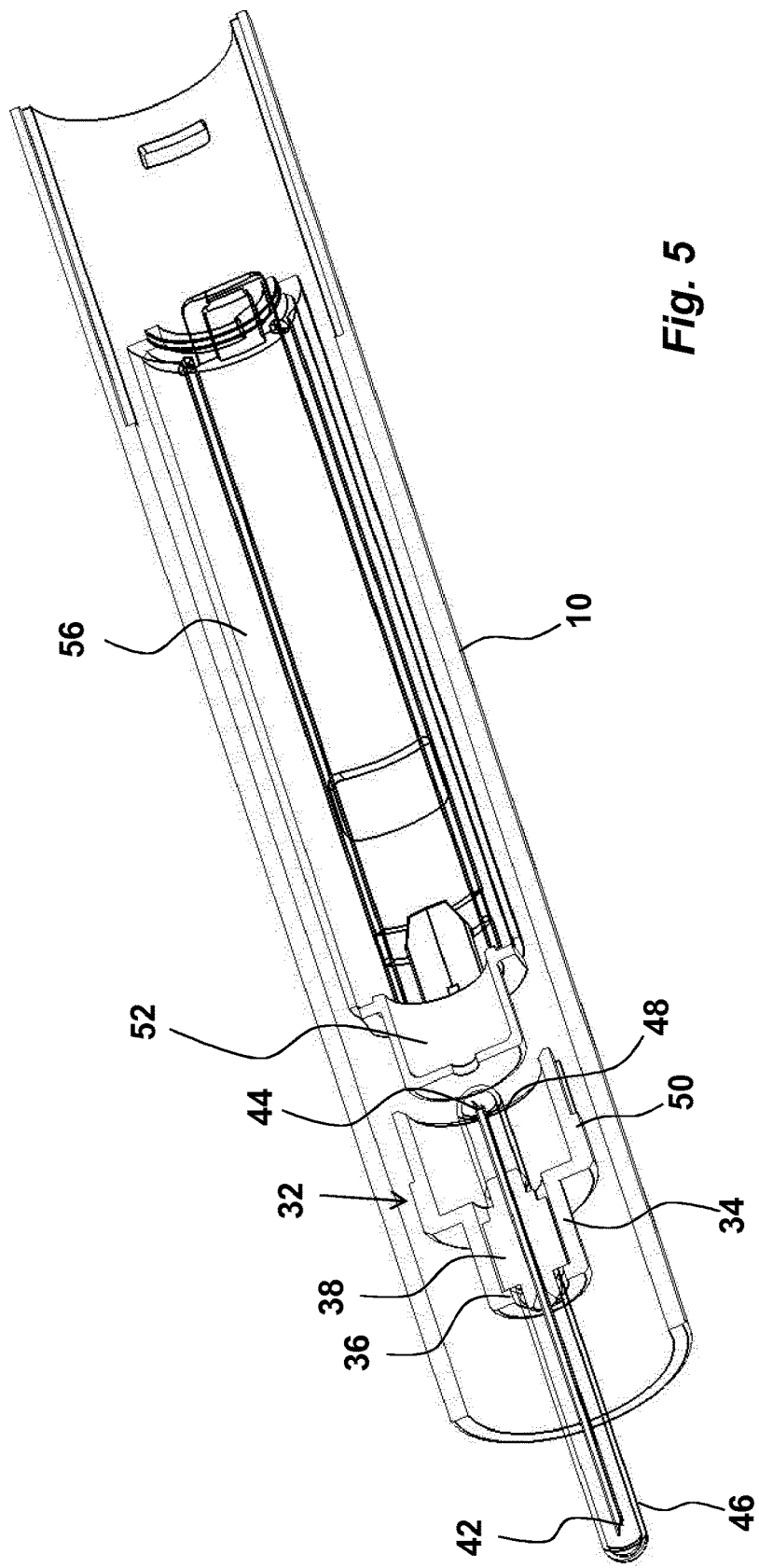

The delivery member 40 is an injection needle assembly comprising a hub 38 wherein an injection needle is arranged with a proximal pointed end 42 and a distal pointed end 44 and wherein the distal pointed end 44 and the proximal pointed end 42 are surrounded and covered with respective protective sheaths 48, 46, FIG. 5. The hub 38 has further a proximally directed ledge and a distally directed ledge and the sheaths 46, 48 are of a suitable flexible material such as rubber or silicone and press-fit on the ledges of the hub 38, for protecting the needle and for keeping the needle sterile before use. The injection needle assembly is fixedly connected to the housing.

A contactor force member 31, which may be a compression spiral spring, is pre-tensioned arranged with a proximal end in contact with a distally directed surface of the transversal end wall 16 for urging the contactor 12 in the proximal direction. The distal end of the contactor force member 31 is in contact with a delivery member holder 32, FIG. 5, arranged in the first housing part 10. The delivery member holder 32 has a first section 34 with a generally tubular shape with distal and proximal openings. The proximal opening is arranged with a circumferential ledge 36. Inside the first section 34, the hub 38 may be positioned. The hub 38 is shaped to fit into the first section 34, preferably with some friction. The delivery member holder 32 is fixedly attached to the first housing part. Alternatively the first housing and the delivery member holder 32 are integral.

A second section 50 of the delivery member holder 32 is also generally tubular and designed such that the distal pointed end 44 of the injection needle 40 protrudes into the interior of the second section 50. The diameter of the second section 50 is chosen such that a neck portion 52 of a proximal section 54 of a medicament container holder 56, FIG. 6, may fit therein. The proximal section 54 of the medicament container holder comprises a circular end wall 58 with two distally extending tongues 60, where the tongues 60 are arranged to be flexible in the radial direction. The free ends of the tongues are arranged with radially outwardly extending ledges 62, which ledges 62 have a wedge-shape as seen in FIG. 7.

Figure 6:
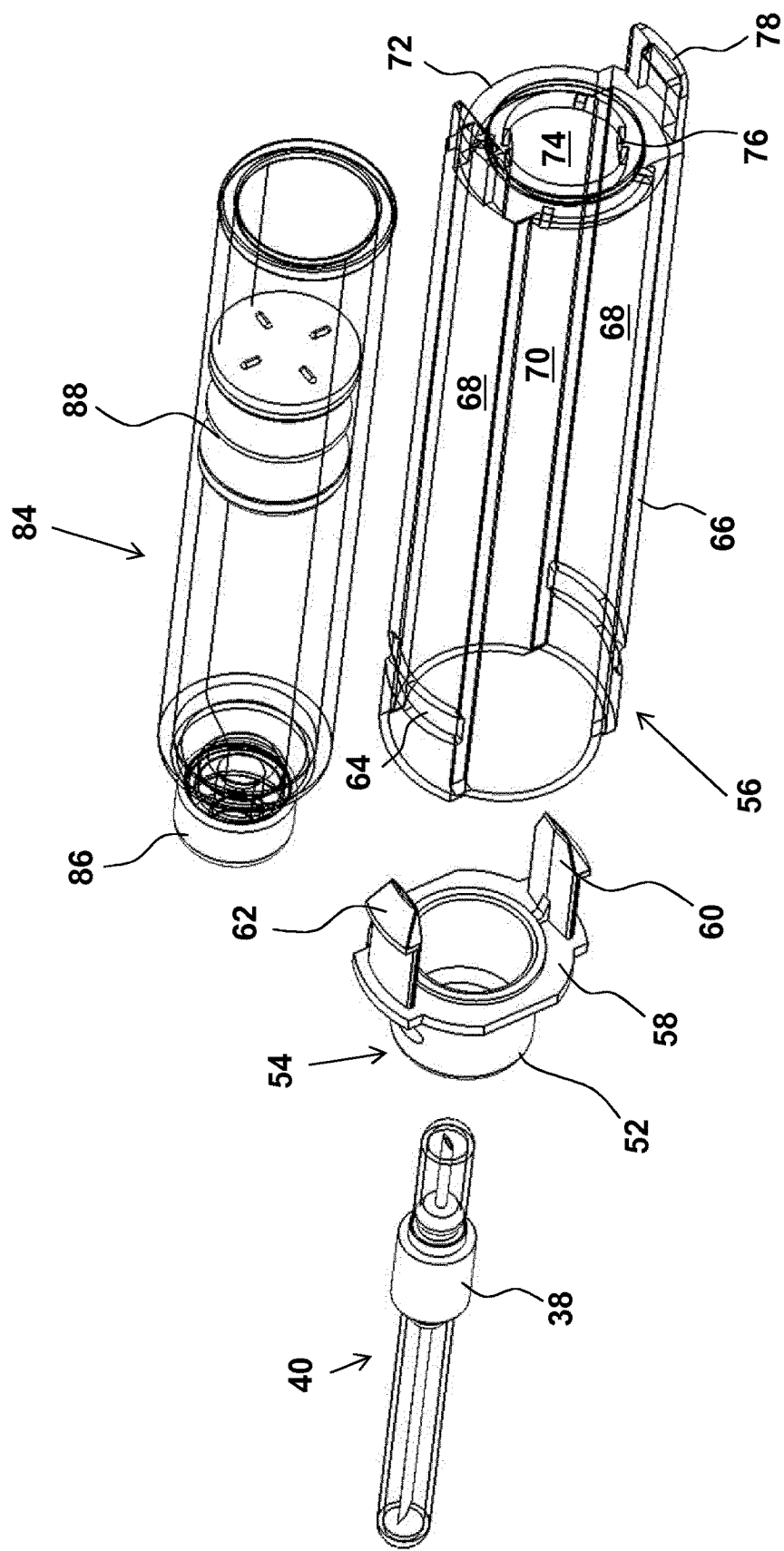
Figure 7:
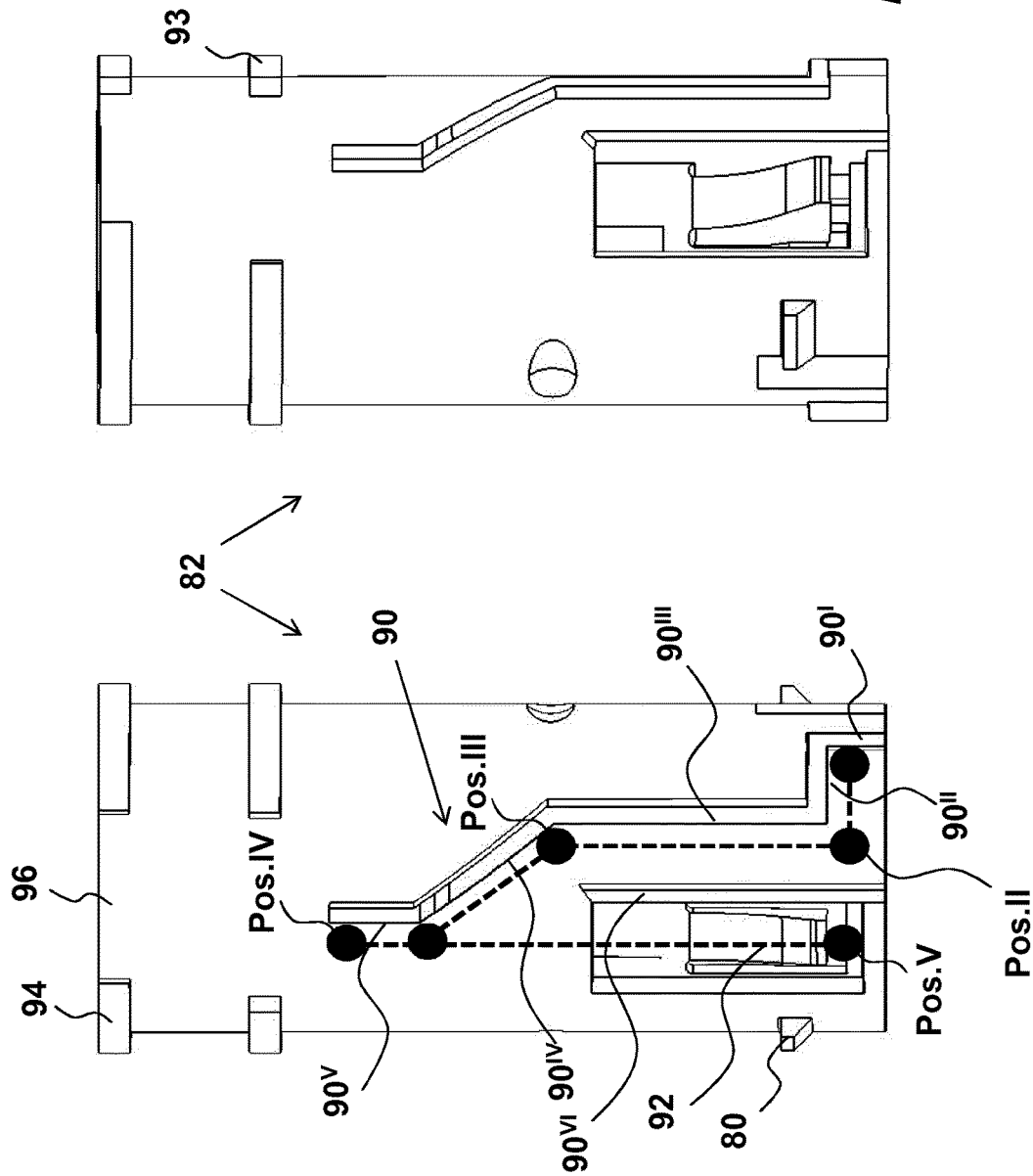

The ledges 62 of the tongues 60 are designed to fit into recesses 64, FIG. 6, arranged in a proximal area of an elongated second section 66 of the medicament container holder 56 such as to connect the two sections with each other. The second section 66 is arranged with two diametrically positioned first wall sections 68 extending from the neck portion and having dimensions and curvature generally corresponding to the inner surface of the first housing part 10. The first wall sections 68 are attached to diametrically positioned second wall sections 70 having dimension such that the arms 18 of the contactor 12 can be accommodated. The distal ends of the first and second wall sections are attached to an end wall 72, which end wall 72 is arranged with a central passage 74. The end wall 72 is arranged with generally inwardly directed protrusions 76 positioned diametrically with respect to each other. The medicament container holder is designed to accommodate the medicament container 84, FIG. 6, provided with a neck portion 86, which neck portion fits into the neck portion 52 of the medicament container holder 56, and is sealed off by a flexible membrane, a septum. The distal end of the medicament container is sealed off by a movable stopper 88.

Further, at the end wall 72 of the second section 66 of the medicament container holder, two distally directed loops 78 are arranged. Each loop comprises a radial inwardly extending protrusion or ledge. Each of the radial inwardly extending protrusion or ledge is arranged such that it may be inter-connected with radial outwardly extending protrusions 80 on an outer surface of the rotator 82, FIG. 7, such that the medicament container holder 56 is held in an initial position in which the medicament container holder 56 with its container is placed such that there is a distance between the distal pointed end 44 of the injection needle 40 and the neck portion of the medicament container, FIG. 3.

Figure 3:
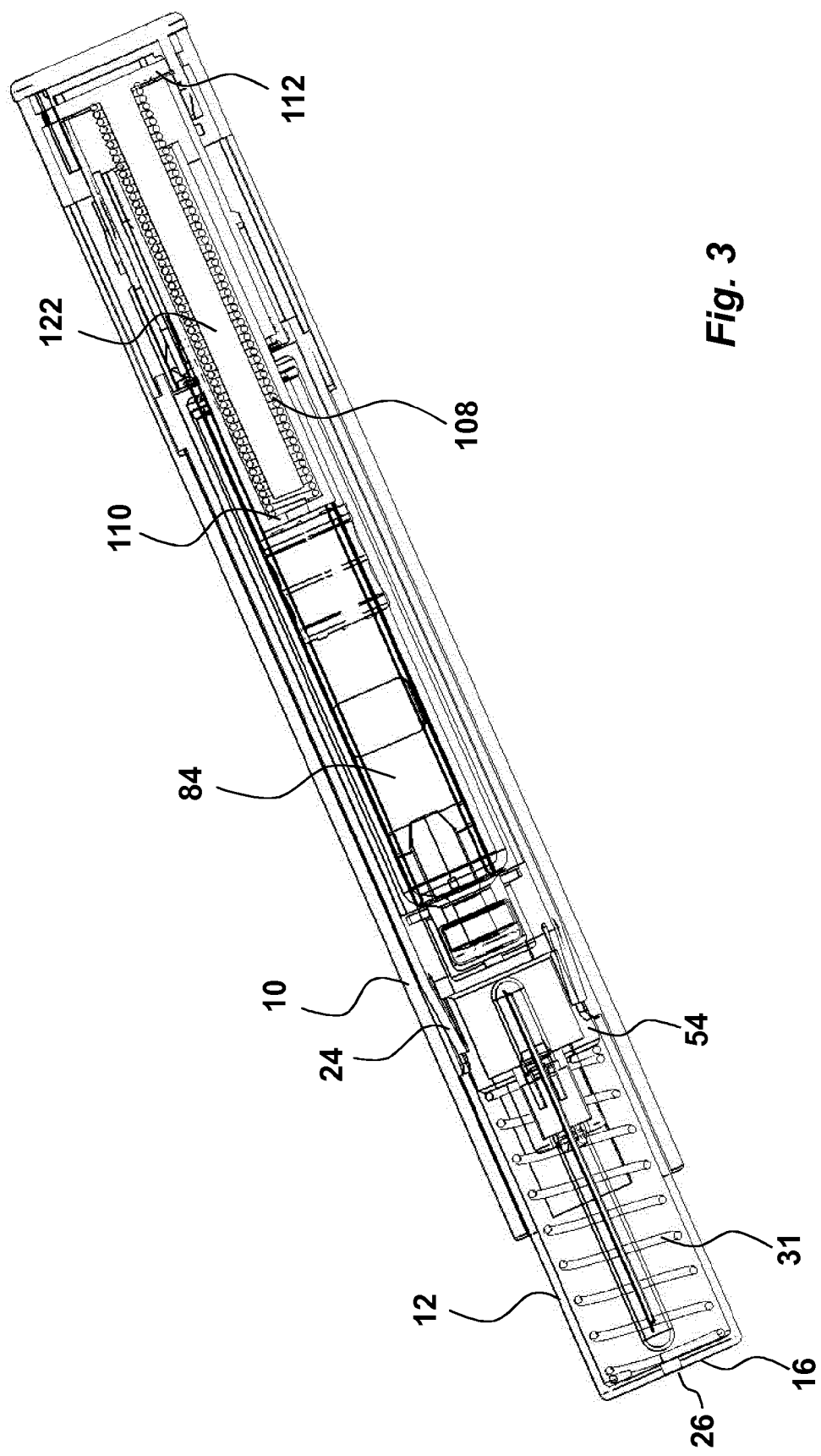
FIG. 3 is a cross-sectional view of the device of FIG. 1, FIGS. 4-10 are detailed views of different components comprised in the device of FIG. 1, FIGS. 11-12 are cross-sectional views of different functional positions of the device of FIG. 1.

In order for the contactor 12 not to be pushed out from the housing in the proximal direction by the contactor force member 31, it is held in position by the tongues 24 of the arms of the contactor being in contact with a distal annular surface of the delivery member holder 32, as seen in FIG. 3.

The second interaction is a further interaction between the contactor and the rotator causing a further interaction between the rotator and the drive mechanism, whereby movement of the contactor from the extended to the retracted position causes a further rotation of the rotator 82 such that the drive mechanism may further act on the container for expelling a dose of medicament through the delivery member. This second interaction will be explained below in detail.

The rotator 82 is a sleeve-shaped member having an outer and an inner surface. The outer surface of the rotator 82 is arranged with a number of outer guiding members of different functions. The outer surface of the rotator 82 is arranged with first outer guiding members 94, FIG. 7, which are transversal circumferential ledges located at a distal end of the rotator 82, and are arranged with cut-outs 96 at two diametrical positions, which cut-outs 96 have a certain width. The functions of the first outer guiding members 94 and cut-outs 96 will be explained below.

The rotator is operably connected to the housing. Preferably, the rotator is rotatably and slidably locked to the housing, more preferably to the second housing part. Thus, the rotator further comprises on it outer surface holding members 93 which are preferably radial outwardly protrusions or ledges configured to interact with corresponding holding members which are preferably radial inwardly protrusions or ledges 115 on the inner surface of the second housing part such that the rotator may rotate in relation to said housing but is prevented to be longitudinally movable.

The outer surface of the rotator 82 is further arranged with second outer guiding members 90. Each second outer guiding member 90 comprises a first outer longitudinal section $90^I$, a first outer transversal and circumferential section $90^{II}$, a second outer longitudinal section $90^{III}$, an outer inclined section $90^{IV}$, a third outer longitudinal section $90^V$, and a fourth outer longitudinal section $90^{VI}$ which is parallel with the first, second and third outer longitudinal sections. The first outer longitudinal section $90^I$ is connected to the first outer transversal and circumferential section $90^{II}$. This section is then connected to the second outer longitudinal section $90^{III}$, which in turn emerges into the outer inclined section $90^{IV}$ continuing in the third outer longitudinal section $90^V$. The fourth outer longitudinal section $90^{VI}$ is parallel with the first, second and third outer longitudinal sections. Adjacent this fourth outer longitudinal section is a first lock member 92 which is a generally radially flexing tongue having a free end pointing in the proximal direction. The shape of the tongue 92 as seen in a side view of FIG. 7 is generally a wedge.

Figure 8:
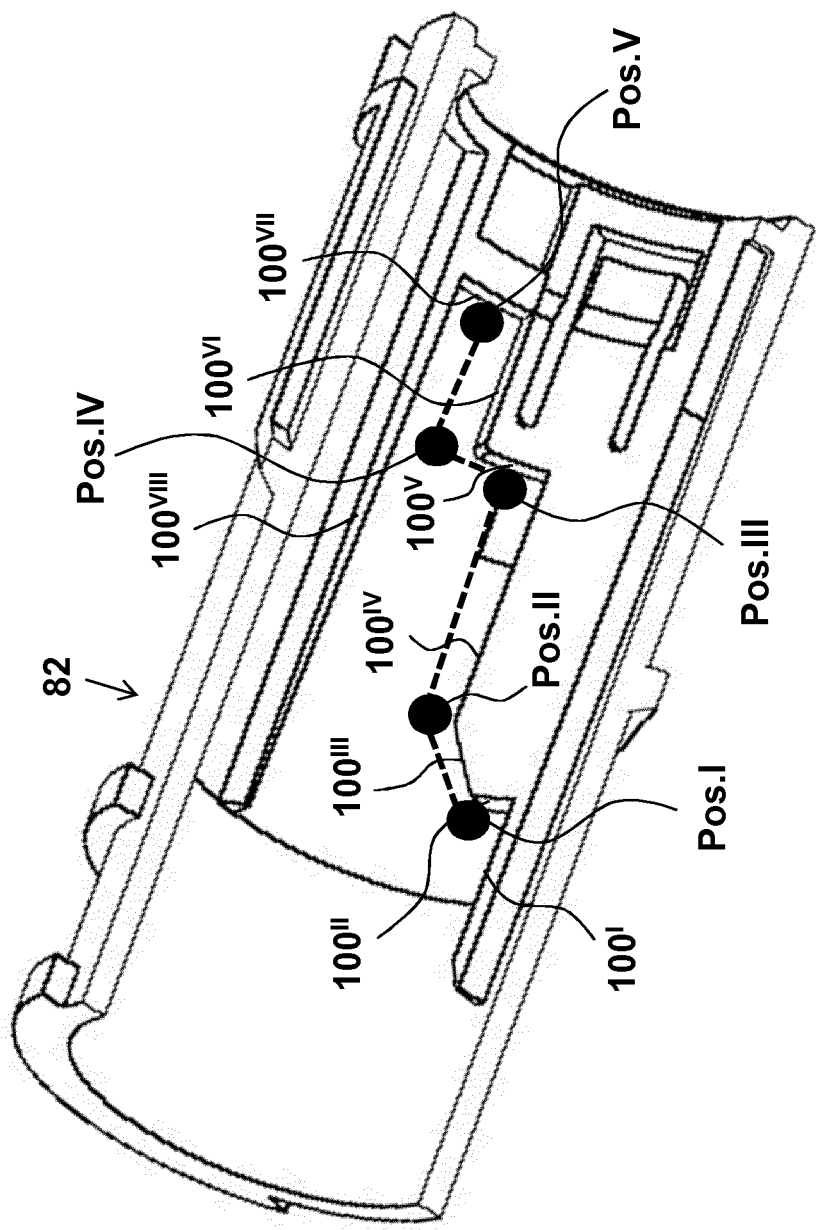

The inner surface of the rotator 82 is arranged with a number of inner guiding members 100 which may be two sets of ledge sections, FIG. 8. Each inner guiding member 100 comprises a first inner longitudinal section $100^I$, a first inner transversal and circumferential section $100^{II}$, an inner inclined section $100^{III}$, second inner longitudinal section $100^{IV}$, a second inner transversal and circumferential section $100^V$, third inner longitudinal section $100^{VI}$, and a third inner transversal and circumferential section $100^{VII}$. The first inner longitudinal section $100^I$ is connected to the first inner transversal and circumferential section $100^{II}$. This section is in turn connected to the inner inclined section $100^{III}$ which is inclined with respect to the longitudinal direction. The inner inclined section $100^{III}$ is connected to the second inner longitudinal section $100^{IV}$, which in turn is connected to the second inner transversal and circumferential section $100^V$. This section is in turn connected to the third inner longitudinal section $100^{VI}$, which terminates with the third inner transversal and circumferential section $100^{VII}$. A long inner longitudinal section $100^{VIII}$, extending in the proximal direction is connected to the third inner transversal and circumferential section $100^{VII}$. The two ledge sections are placed diametrically opposed on the inner surface of the rotator.

Figure 9:
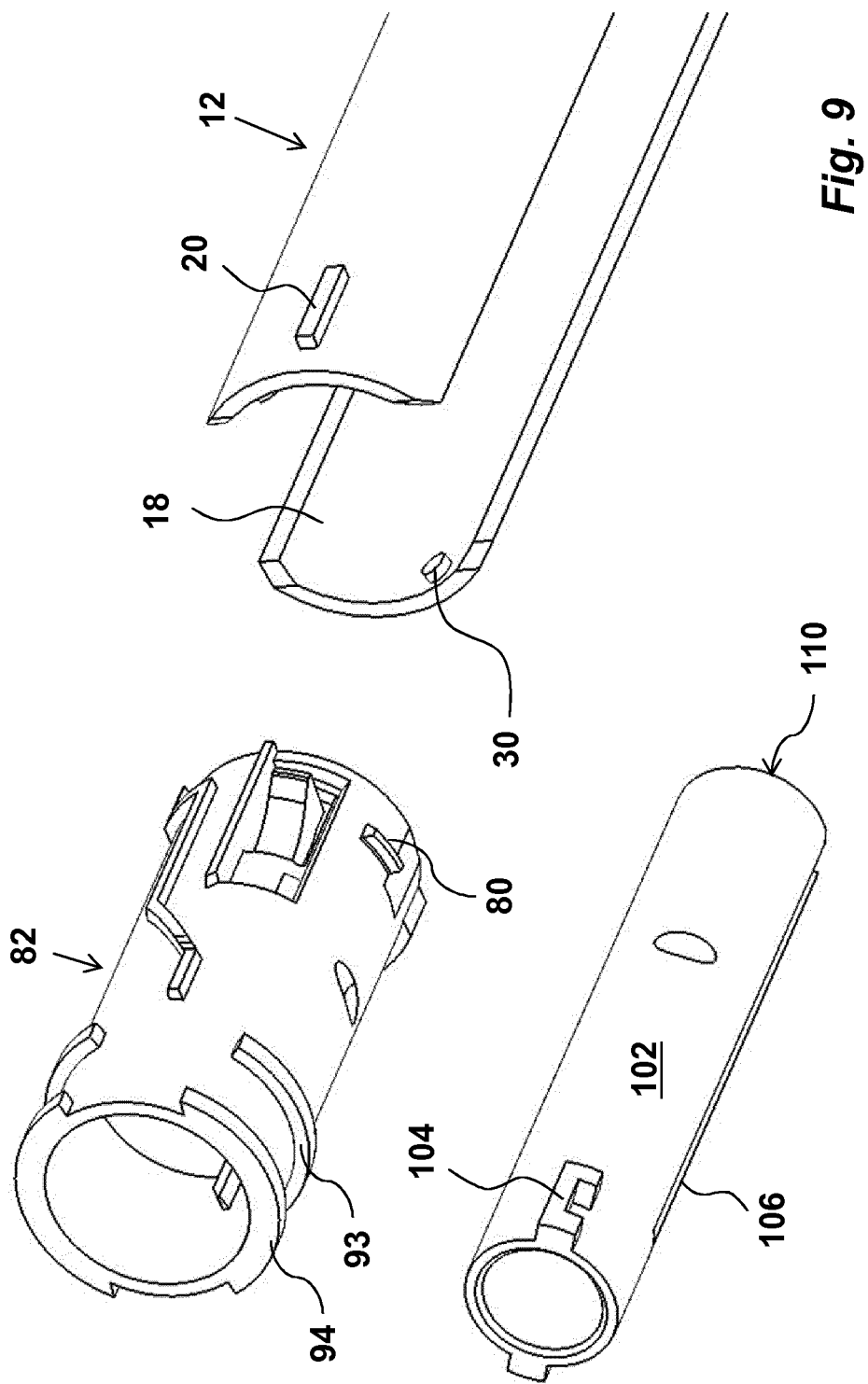

A generally elongated tubular plunger rod 102 comprised in a drive mechanism, FIG. 9, is coaxially arranged through the rotator 82. The plunger rod 102 is initially positioned such that a proximal end thereof is in contact with the stopper 88 of the medicament container 84. The plunger rod 102 comprises a number of first contact members 104 which may be two generally radially outwardly extending protrusions. These first contact members 104 are intended to interact with the inner guiding members 100 on the inner surface of the rotator 82. The plunger rod 102 is further arranged with two longitudinally extending grooves 106. These grooves 106 are intended to interact with the protrusions 76 of the central passage 74 of the second section 66 of the medicament container holder 56, such that a rotational lock is obtained between the two while allowing relative longitudinal movement. The plunger rod is a hollow rod and inside the plunger rod 102 a force member 108 is positioned, also comprised in the drive mechanism, FIGS. 2 and 3. The force member 108 is in the embodiment shown as a compression spiral spring having a proximal end in contact with an end wall 110 at the proximal end of the plunger rod. A distal end of the force member 108 is in contact with a wall section 112 of the second housing part 114, FIG. 4. The force member 108 is pre-tensioned and has a predetermined load force configured to act on the plunger rod. Thus, the first contact members 104 of the plunger rod 102 are configured to interact with the inner guiding members 100 of the rotator 82 for holding the plunger rod in an initial state, an intermediate state and in a final state depending on the rotational position of the rotator 82.

In the shown embodiment, the second housing part 114 is intended to be connected to the distal end of the first housing part and is arranged with two proximally directed arms 116, where each arm is arranged with a generally radially flexible tongue 118, having a free end in the distal direction. The tongues 118 are arranged with outwardly directed ledges, which ledges are intended to fit into cut-outs 120 on a distal area of the first housing part 10, for locking the two housing parts together. The end wall 112 of the second housing part 114 is arranged with a proximally directed spring guide rod 122, intended to guide and support the force member 108. The end wall 112 of the second housing part 114 is further arranged with a number of passages 124, in the embodiment shown two passages arranged diametrically. The outer surface of the second housing part is further arranged with two diametrically opposed recesses 126.

In the shown embodiment, the safety member 128 is releasably attached to the second housing part. It comprises an end wall 130. On the end wall 130, two proximally directed grip panels 132 are arranged, which grip panels 132 are intended to fit into the recesses 126 of the second housing part 114. The safety member 128 further comprises second contact members 134, which are two arms attached to the end wall 130, also being directed in the proximal direction. These second contact members 134 are intended to fit into the passages 124 of the second housing part 114 and in the cut-outs 96 of first outer guiding members 94 of the rotator 82. The second contact members 134 are arranged with side edges 136 having a curved shape as seen in FIG. 4, providing a side-directed protrusion. The function of the shape of the second contact members will be explained below.

The device is intended to function as follows. When delivered to the user, the device is preferably assembled and ready to use. This means that the delivery member 40, here an injection needle is fitted into the holder 32 of the first housing part 10 and a medicament container 84 has been placed in the medicament container holder 56. In the initial position, the medicament container holder 56 with its container is placed such that there is a distance between the distal pointed end 44 of the injection needle 40 and the neck portion of the medicament container, FIG. 3.

Figure 10:
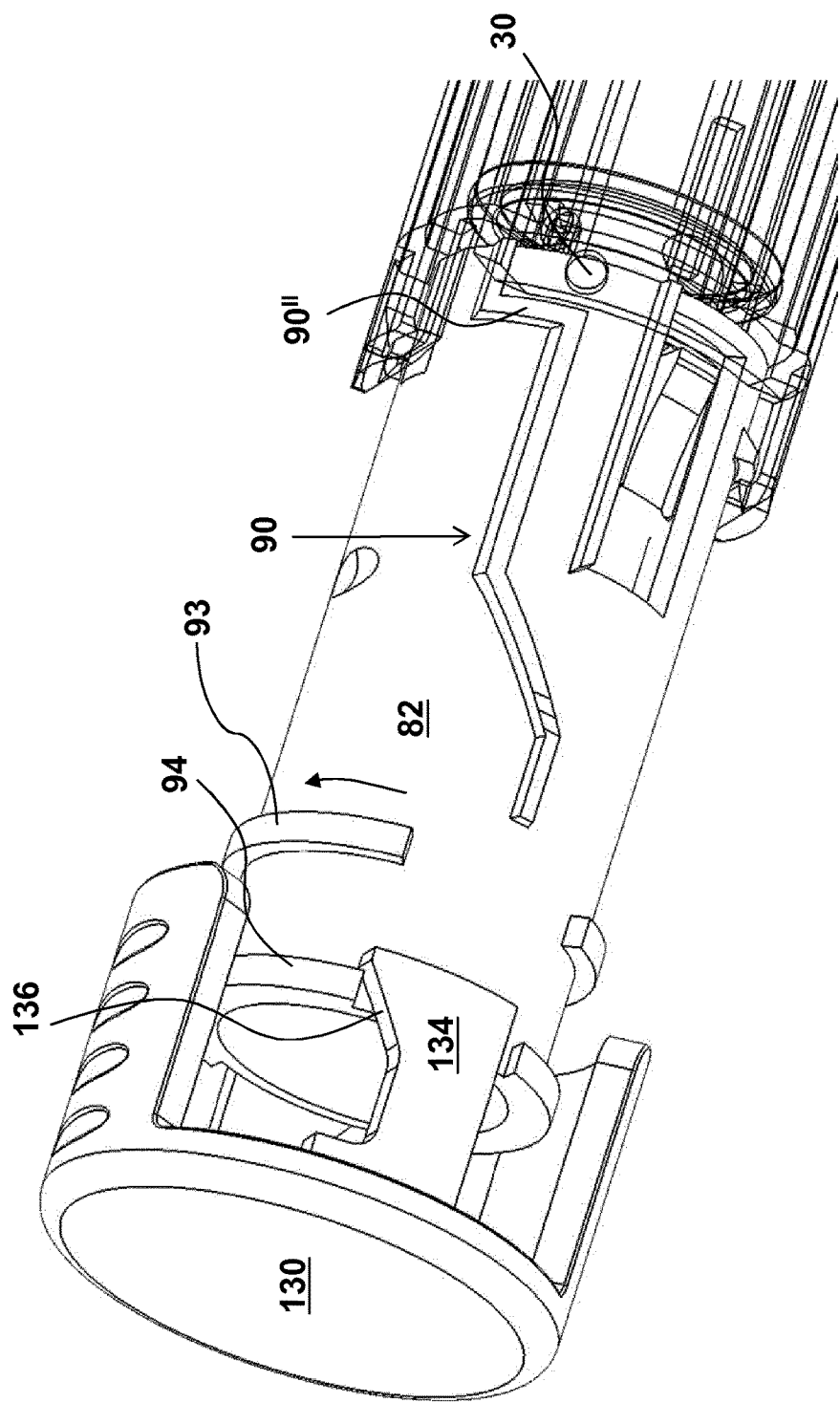

Further, the safety member 128 is attached to the second housing part 114. The contactor 12 is in the extended position urged by the contactor force member 31. Also, the contactor 12 is locked from being moved from the extended to the retracted position in relation to the first housing part due to the interaction between the third contact members 30 of the contactor 12 and the first outer transversal and circumferential section 90$^{II}$ of the second outer guiding members 90 on the outer surface of the rotator 82, as seen in FIG. 10, wherein the first outer transversal and circumferential section 90$^{II}$ will function as a blocking member. The plunger rod 102 is held in the initial state due to the interaction between each of the first contact members 104 of the plunger rod 102 and each of the first inner transversal and circumferential sections 100$^{II}$ of the inner guiding members 100 on the inner surface of the rotator 82 as seen in FIG. 8, pos. I. until the rotator 82 is turned when the safety member 128 is removed.

When the device is to be used, the safety member 128 is removed from the device by a user gripping the grip panels 132 and longitudinally pulling the safety member 128 in the distal direction. Thereby the second contact members 134 are also longitudinally moved in the distal direction and the curved side surfaces 136 which are in contact with an end surface of the first outer guiding members 94 as seen in FIG. 10, forces the rotator 82 to rotate a certain rotational angle. At the same time, the rotation of the rotator 82 when removing the safety member 128 causes the first contact members 104 of the plunger rod 102 to be released or to be moved from the initial state where they leave the contact with the first inner transversal and circumferential section 100$^{II}$ of the inner guiding member 100 on the inner surface of the rotator 82 and come in contact with the inner inclined section 100$^{III}$ as seen in FIG. 8, pos. II. The plunger rod 102 is then forced to move proximally by the force member 108, and the contact with the inner inclined surface 100$^{III}$ will cause the rotator 82 to rotate a further angle such that the radial inwardly extending protrusions or ledges of the loops 78 are released from the radial outwardly extending protrusions 80 on the outer surface of the rotator 82.

Figure 11:
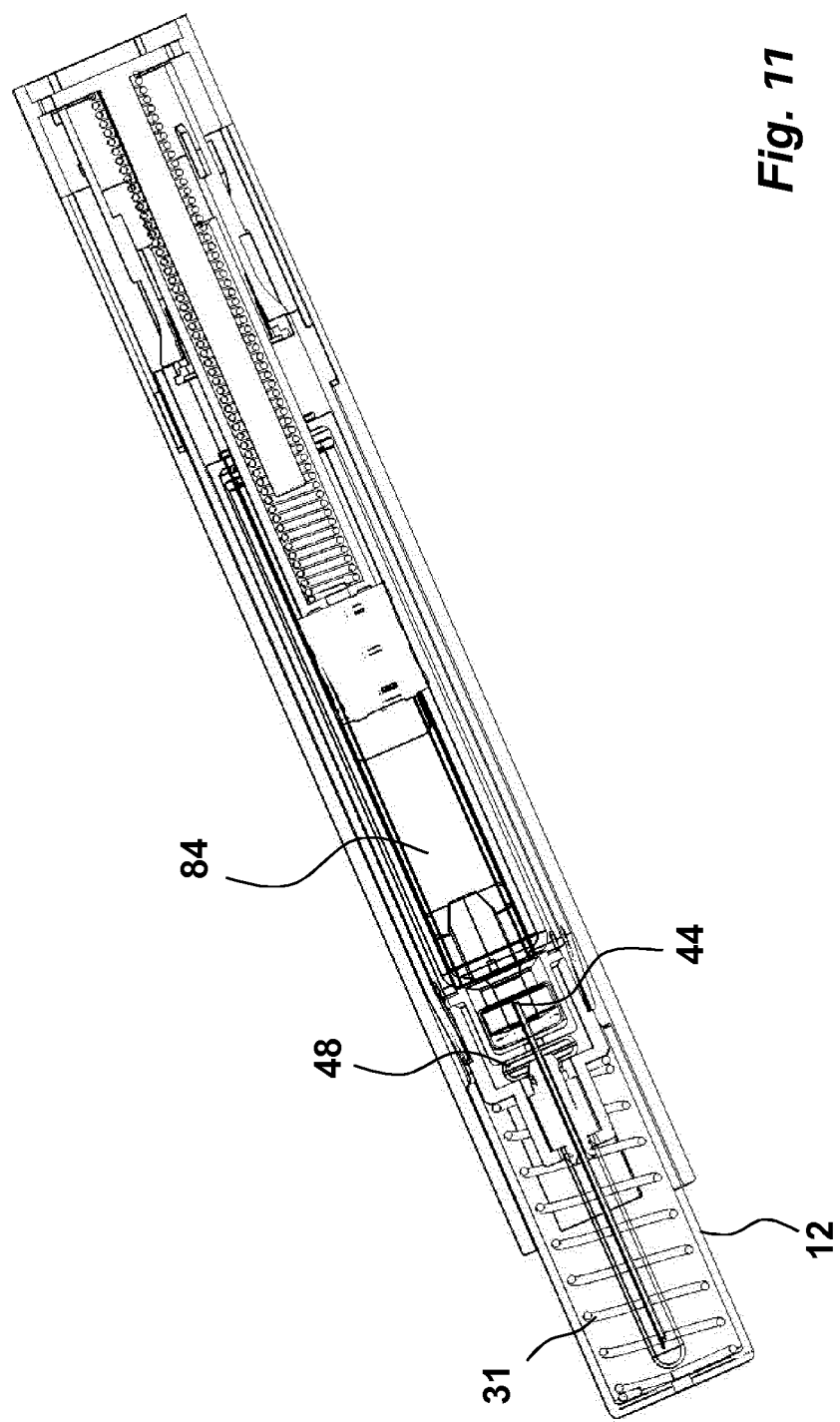

During the movement of the plunger rod 102 from the initial state to the intermediate state, the plunger rod act with a force on the stopper 88 of the medicament container 84 such that the medicament container 84 and the medicament container holder 56 move as a unit in the proximal direction. In the embodiment shown, this movement now causes the distal pointed end 44 of the injection needle 40 to first penetrate the protective sheath 48 and then a septum at the neck portion of the medicament container 84, while compressing the protective sheath 48 surrounding the distal end of the needle, FIG. 11.

When the septum is penetrated by the distal end 44 of the needle, a passage from the container is opened by the injection needle 40 and the pressure is released, causing a priming of the medicament container 84. Air, and possibly a small amount of medicament, will then be expelled into the interior of the protective sheath 46 surrounding the proximal end of the injection needle 40.

The movement of the plunger rod 102 is stopped when the first contact members 104 hit the second inner transversal and circumferential section 100, FIG. 8, pos. III. The plunger rod 102 has moved from the initial state to the intermediate state. The plunger rod 102 is held in the intermediate state due to the interaction between each of the first contact members 104 of the plunger rod 102 and each of the second inner transversal and circumferential sections 100$^{V}$ of the inner guiding members 100 on the inner surface of the rotator 82.

Further, the rotation of the rotator 82 causes the first outer guiding members 94 to move to a position in front of the passages 124 of the second housing part. Any attempts to reintroduce the second contact members 134 of the safety member 128 into the passages 124 of the second housing part 114 are thereby prevented. Thus, the first outer guiding members 94 on the rotator prevent re-connection of the safety member 128 after removal of the safety member and turning of the rotator.

Also, the above described rotation of the rotator 82 has now moved the first outer transversal and circumferential sections 90$^{II}$ out of contact with the third contact members 30 of the contactor 12, as seen in FIG. 7, pos. II, whereby the latter is free to move in the distal direction from the extended position to the retracted position.

Figure 12:
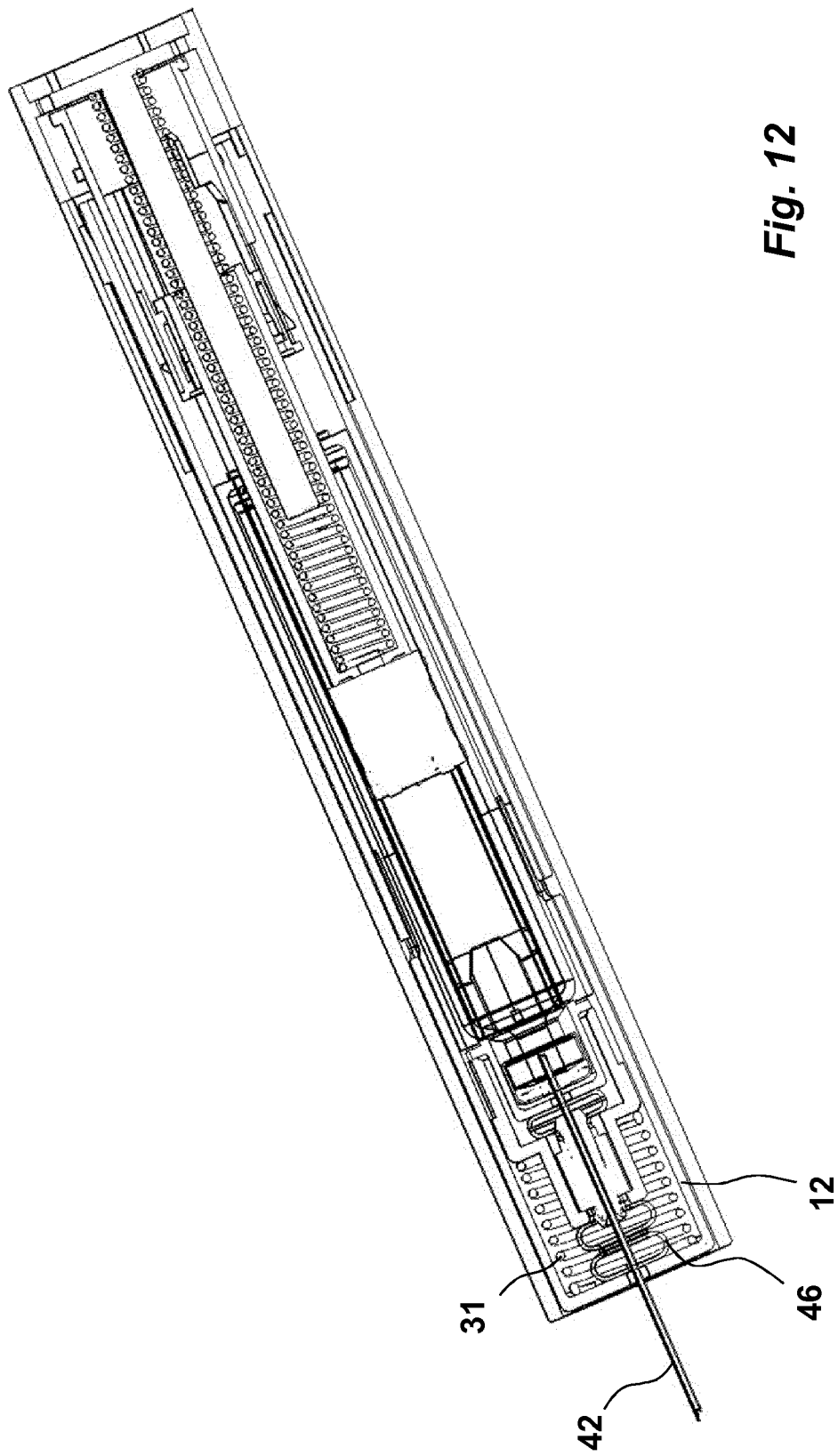

The next step is then to perform a manual penetration or semi-penetration such that the contactor moves in relation to the delivery member to expose the proximal pointed end 42 of the injection needle. The transversal end wall 16 of the contactor is positioned on a delivery site i.e. an injection site and the contactor 12 is thereby pressed against the delivery site, whereby the contactor 12 will be moved, relative to the housing, in the distal direction from the extended position to the retracted position whereby the contactor force member 31 is compressed. In the embodiment shown, the proximal end of the injection needle will then penetrate the proximal protective sheath 46 and pass through the passage 26 on the transversal end wall 16 of the contactor and into the tissue of a user, FIG. 12. When the contactor is moved from the extended position to the retracted position, each of the third contact members 30 of the contactor 12 will first pass along each of the second outer longitudinal sections 90$^{III}$ and then come in contact with each of the outer inclined sections 90$^{IV}$, FIG. 7, pos. III.

The interaction between the third contact members 30 of the contactor 12 and the outer inclined sections 90$^{IV}$ forces the rotator 82 to be further turned/rotated a certain angle. This further rotation allows the plunger rod to move from the intermediate state in which the plunger rod is held due to the interaction between each of the first contact members 104 of the plunger rod 102 and each of the second inner transversal and circumferential sections 100$^{V}$ of the inner guiding members 100 on the inner surface of the rotator 82, to a final state in which the plunger rod is prevented from moving further due to the interaction between each of the first contact members 104 of the plunger rod 102 and each of third inner transversal and circumferential section 100$^{VII}$ of the inner guiding members 100 on the inner surface of the rotator 82. This movement causes the stopper 88 of the medicament container 84 to be moved in the proximal direction, from pos. IV to pos. V, whereby a dose of medicament is expelled through the delivery member 40 at the delivery site. As described above, the delivery is stopped when the first contact members 104 of the plunger rod 102 are moved in contact with the third inner transversal and circumferential section 100$^{VII}$, FIG. 8, pos. V.

The device may then be removed from the delivery site whereby the contactor force member 31 will urge the contactor 12 in the proximal direction, relative to the housing, from the retracted position to the extended position. At the same time, the third contact members 30 of the contactor will move axially along the rotator, FIG. 7, until they pass the first lock members 92 of the rotator, pos. V, FIG. 7. The lock members 92 will flex radially inwards as the third contact members pass from pos. IV to pos. V. Afterwards they will flex back and their wedge shape prevents the contactor 12 from being moved again in the distal direction from the extended to the retracted position. Thus, the delivery member 40, i.e. an injection needle, is hidden and protected inside the contactor, preventing any accidental needle sticks. The device may now be discarded.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
   a housing having a proximal end and a distal end;
   a delivery member connected to the housing;
   a medicament container operably arranged within the housing;
   a drive mechanism configured to act on the medicament container for priming and for expelling a dose of medicament; and
   an activator mechanism configured to interact with the drive mechanism, wherein the activator mechanism comprises:
   a contactor axially movable in relation to the housing between an extended position in which the delivery member is hidden and protected by the contactor and a retracted position in which the delivery member is exposed;
   a rotator operably arranged inside the housing and operably connected to the contactor and to the drive mechanism, wherein the rotator in an initial position locks the contactor in the extended position;
   a safety member operably connected to the rotator such that removal of the safety member causes rotation of the rotator from the initial position, thereby activating the drive mechanism to act on the container for priming the container; wherein activation of the drive mechanism causes further rotation of the rotator such that the contactor is unlocked;
   whereby movement of the contactor when unlocked from the extended position to the retracted position causes additional rotation of the rotator that enables the drive mechanism to act on the medicament container for expelling the dose of medicament through the delivery member.

2. The medicament delivery device of claim 1, wherein the contactor is operably arranged to the housing at the proximal end.

3. The medicament delivery device of claim 1, wherein the drive mechanism comprises a plunger rod and a force member having a predetermined load force configured to act on the plunger rod.

4. The medicament delivery device of claim 3, wherein the plunger rod comprises a number of first contact members and the rotator comprises a number of inner guiding members that interact with the first contact members to hold the plunger rod in an initial state, an intermediate state, and a final state depending on rotational angle of the rotator.

5. The medicament delivery device of claim 4, wherein each of the inner guiding members comprises a first inner longitudinal section, a first inner transversal and circumferential section, an inner inclined section, a second inner longitudinal section, a second inner transversal and circumferential section, a third inner longitudinal section, and a third inner transversal and circumferential section.

6. The medicament delivery device of claim 5, wherein the plunger rod is held in the initial state due to interaction between each of the first contact members of the plunger rod and each of the first inner transversal and circumferential sections of the inner guiding members on an inner surface of the rotator until the rotator is turned when the safety member is removed.

7. The medicament delivery device of claim 5, wherein the contactor comprises a number of third contact members and the rotator further comprises second outer guiding members configured to interact with the third contact members.

8. The medicament delivery device of claim 7, wherein each of the second outer guiding members comprises a first outer longitudinal section, a first outer transversal and circumferential section, a second outer longitudinal section, an outer inclined section, a third outer longitudinal section, and a fourth outer longitudinal section that is parallel to the first, second, and third outer longitudinal sections.

9. The medicament delivery device of claim 8, wherein each of the third contact members is configured to interact with each of the first outer transversal and circumferential sections of the second outer guiding members on an outer surface of the rotator such that the contactor is locked from movement until the rotator is turned when the safety member is removed.

10. The medicament delivery device of claim 8, wherein the safety member comprises second contact members configured to cooperate with first outer guiding members on the rotator to turn the rotator, upon removal of the safety member, a certain rotational angle such that the plunger rod is released from the initial state to an intermediate state for priming the medicament container.

11. The medicament delivery device of claim 10, wherein the plunger rod is held in the intermediate state by interaction between each of the first contact members and each of the second inner transversal and circumferential sections of the inner guiding members on an inner surface of the rotator.

12. The medicament delivery device of claim 10, wherein the first outer guiding members on the rotator prevent re-connection of the safety member after removal of the safety member and turning of the rotator.

13. The medicament delivery device of claim 11, wherein the contactor comprises a number of third contact members and the rotator further comprises second outer guiding members configured to interact with the third contact members; the third contact members interact with outer inclined sections of the second outer guiding members, whereby movement of the contactor from the extended position to the retracted position causes further rotation of the rotator a certain rotational angle such that the plunger rod is released from the intermediate state to the final state, thereby expelling the dose of medicament through the delivery member.

14. The medicament delivery device of claim 13, wherein the plunger rod is held in the final state due to interaction between each of the first contact members of the plunger rod and each of the each of third inner transversal and circumferential sections of the inner guiding members on an inner surface of the rotator.

15. The medicament delivery device of claim 14, wherein the rotator further comprises first lock members configured to interact with the third contact members of the contactor such that the contactor is locked from axial movement after the dose of medicament is expelled through the delivery member and the contactor is moved from the retracted position to the extended position.

16. The medicament delivery device of claim 1, wherein the delivery member comprises an injection needle assembly fixedly connected to the housing and including a hub and an injection needle having a proximal pointed end and a distal pointed end; and the distal pointed end and proximal pointed end are surrounded and covered with respective protective sheaths.

17. The medicament delivery device of claim 16, wherein the protective sheath covering the distal pointed end is pierced and compressed during movement of the medicament container.

18. The medicament delivery device of claim 17, wherein the protective sheath covering the proximal pointed end is pierced and compressed during movement of the contactor from the extended position to the retracted position such that the proximal pointed end of the injection needle is exposed.

19. The medicament delivery device of claim 1, further comprising a medicament container holder movably disposed inside the housing and configured to accommodate the medicament container.

\* \* \* \* \*